(12) United States Patent
Chen et al.

(10) Patent No.: US 7,205,011 B2
(45) Date of Patent: Apr. 17, 2007

(54) ANTI-INFLAMMATORY ACTIVITY OF A SPECIFIC TURMERIC EXTRACT

(75) Inventors: Guan Jie Chen, Tucson, AZ (US); Robert Clark Lantz, Tucson, AZ (US); Aniko M. Solyom, Tucson, AZ (US); Barbara N. Timmermann, Tucson, AZ (US); Shivanand D. Jolad, Tucson, AZ (US)

(73) Assignee: Board of Regents, Acting for and on behalf of, University of Arizona, Tucson, AZ (US)

( * ) Notice: Subject to any disclaimer, the term of this patent is extended or adjusted under 35 U.S.C. 154(b) by 0 days.

(21) Appl. No.: 10/989,874

(22) Filed: Nov. 15, 2004

(65) Prior Publication Data

US 2005/0123632 A1 Jun. 9, 2005

Related U.S. Application Data

(60) Provisional application No. 60/520,028, filed on Nov. 14, 2003.

(51) Int. Cl.
*A61K 36/906* (2006.01)

(52) U.S. Cl. .................. 424/756; 514/825; 514/885; 514/886

(58) Field of Classification Search ...................... None
See application file for complete search history.

(56) References Cited

U.S. PATENT DOCUMENTS

| | | | |
|---|---|---|---|
| 5,667,791 A | 9/1997 | Hersh et al. | |
| 6,337,320 B1 | 1/2002 | Hersh et al. | |
| 6,416,808 B1 | 7/2002 | Crea | |
| 6,437,004 B1 | 8/2002 | Perricone | |

FOREIGN PATENT DOCUMENTS

| | | | |
|---|---|---|---|
| WO | WO-00/00183 | 1/2000 | |
| WO | WO-00/36936 | 6/2000 | |
| WO | WO 01/30335 A2 * | 5/2001 | |
| WO | WO-01/91589 | 12/2001 | |

OTHER PUBLICATIONS

Abe et al., "Curcumin inhibition of inflammatory cytokine production by human peripheral blood mono . . . ", Pharmacol. Res. 1999, 39: 41-47.
Aggarwal et al., "Anticancer potential of curcumin; preclinical and clinical studies.", Anticancer Res. 2003, 23: 363-398.
Chan et al., "In vivo inhibition of nitric oxide synthase gene expression by . . . ", Biochemical Pharmacology, 55:1995-1962, 1998.
Chan, "Inhibition of Tumor necrosis factor by curcumin", Biochem Pharmacol, 49, pp. 1551-1556, 1995.
Chen et al., "Inhibition of the c-Jun N-terminal kinase (JNK) signaling pathway by curcumin.", Oncogene. 1998, 17: 173-178.
Gallin et al., "Overview in inflammation: basic principles and clinical correlates", 3rd Ed., Lippincott Williams & Wilkins, Philadelphia, 1999, pp. 1-3.
Goel, et al., "Specific inhibition of cyclooxygenase-1 (COX-2) expression by dietary curcumin in HT-29 human colon cancer cells.", Cancer Let., 2001, 172:111-118.
Hong et al., "Evaluation of natural products on inhibition of inducible cyclooxygenase . . . ", Ethnopharmacol. 2002 83:153-159.
Hong et al., "Inhibitory effects of natural sesquiterpenoids isolated from rhizomes of *Curcuma zedoaria* on prostaglandin E2 . . . ", Planta Medica 2002 68:545-547.
Jobin et al., "Curcumin blocks cytokine-mediated NF-kappa B activation and proinflammatory . . . ", J Immunology, 1999, 163: 3474-3483.
Joe et al., "Effect of curcumin and capsaicin on arachidonic acid metabolism and lysosomal enzyme . . . ", Lipids, 1997, 32: 1173-1180.
Kelloff et al., "Strategy and planning for chemopreventive drug development: clinical developmant plans II.", J. Cellular Biochem—Supplement, 1996, 26:54-71.
Kim et al., "Curcuminoids from *Curcuma longa* L. (*Zingiberaceae*) that protect PC12 rat . . . ", Neurosci. Let., 2001 303:57-61.
Lee et al., "Suppressive effect of natural sesquiterpenoids on inducible cyclooxygenase . . . ", J. Environ. Pathol. Toxicol. Oncol., 2002, 21:141-148.
Pan et al., "Comparative studies on the suppression of nitric oxicd synthase by . . . ", Biochem. Pharmacol, 2002, 60:1665-1676.
Plummer et al., "Inhibition of cyclo-oxygenase 2 expression in colon cells by the . . . ", Oncogene, 1999, 18:6013-6020.
Ramsewak et al., "Cytotoxicity, antioxidant and anti-inflammatory activities of curcumins I-III from *Curcuma longa*. ", Phytomedicine, 2000, 7:303-308.
Ruby et al., "Anti-tumor and antioxidant activity of natural curcuminoids.", Cancer Letters, 1995, 94:79-83.
Singh et al., "Activation of transcription factor NF-kB is suppressed by curcumin (diferulolylmethane).", 1995, J. Biol. Chem. 270: 24995-25000.
Wang,J., et al., "Stability of curcumin in buffer solutions and characterization of its degradation products." J. Pharmaceut. Biomed. Anal., 1997, 15:1867-76.
Zhang, "Curcumin inhibits cyclooxygenase-2 transcription in bile acid—and phorbol ester . . . ", Carcinogenesis, 1999, 20:445-451.

* cited by examiner

Primary Examiner—Christopher R. Tate
(74) Attorney, Agent, or Firm—Quarles & Brady LLP

(57) ABSTRACT

Disclosed herein are mixtures of turmeric extract oils. One mixture of turmeric oils is the hexane soluble fraction obtained by dissolving turmeric powder in hexane to form a hexane mixture, filtering the hexane mixture and evaporating the hexane from the turmeric oil mixture. A more refined turmeric oil combination is the oil left after the turmeric oil mixture is dissolved in hexane, placed on a silica gel/hexane chromatography column, and eluted with hexane into fractions that were then evaporated, thereby leaving the refined turmeric oil combination. Also disclosed are methods for treating inflammation, arthritis and rheumatoid arthritis and a pharmaceutical dosage form of the refined turmeric oil combination.

7 Claims, 3 Drawing Sheets

ANTI-INFLAMMATORY ACTIVITY OF A SPECIFIC TURMERIC EXTRACT

CROSS-REFERENCE TO RELATED APPLICATIONS

This application claims the benefit of U.S. Provisional Application Ser. No. 60/520,028, filed Nov. 14, 2003.

STATEMENT REGARDING FEDERALLY SPONSORED RESEARCH

This invention was made with government support under Grant No. P50 AT00474 awarded by the National Institute of Health. The United States Government has certain rights in this invention.

TECHNICAL FIELD

The present invention is relevant to the field of anti-inflammatory compounds and anti-oxidants and the isolation from plants of anti-inflammatory compounds and anti-oxidants.

BACKGROUND ART

The use of dietary supplements containing botanical products is rapidly expanding in the United States. In the mass market alone, over $650 million is spent yearly on botanical supplements. The public is using these products for a wide range of health-related problems, including chronic inflammatory diseases such as chronic obstructive pulmonary disease, asthma and rheumatoid arthritis. Yet, firm scientific information about botanicals and their active ingredients is not currently available. Used for centuries in Ayurvedic medicine, a number of these botanical supplements have been purported to have anti-inflammatory actions.

Turmeric, the powdered rhizome of the herb *Curcuma longa* L. (Zingiberaceae), has been used extensively in curries and mustards as a coloring and flavoring agent. Powdered turmeric, or its extract, is found in numerous commercially available botanical supplements. In Ayurvedic medicine turmeric has traditionally been used to treat inflammation, skin wounds and tumors. (Ammon and Wahl, 1991, Planta Med., 57:1–7). Turmeric extracts have been reported to have antimicrobial, anti-inflammatory, antioxidant and anticancer effects. In preclinical animal studies turmeric has shown anti-inflammatory, cancer chemopreventive and anti-neoplastic properties (Kelloff et al., 1996, J. Cell. Biochem. Supplement 26:54–71). The best characterized of the compounds found in turmeric is curcumin, which has been shown to reduce inflammation.

Inflammation is associated with a large collection of mediators that initiate the inflammatory response, recruit and activate other cells to the site of inflammation and subsequently resolve the inflammation (Gallin and Snyderman, 1999, Overview in INFLAMMATION: BASIC PRINCIPLES AND CLINICAL CORRELATES, 3 d ed., Lippincott Williams & Wilkins, Philadelphia, pp. 1–3). Cytokines are regulatory polypeptides that are produced by virtually all cells (For review, see THE CYTOKINE HANDBOOK, 1998, ed by A. Thomson, 3d edition, Academic Press, New York City). In general, cytokines are not constitutively produced. However, in the presence of appropriate stimuli (for example, lipopolysaccharide (LPS) from gram negative bacteria), increased gene expression and production of cytokines occurs, leading to the initiation of an inflammatory response. Two major cytokines involved in the initiation of inflammation are tumor necrosis factor α (TNF-α) and interleukin 1 (IL-1). These proteins have multiple sites of action. Responses include induction of other cytokines, activation of arachidonic acid metabolism, priming of polymorphonuclear leukocytes (PMN), and up-regulation of adhesion molecules. Regulation of gene expression for these cytokines is in part controlled by activation of transcription factors such as nuclear factor of K light chain B (NF-κB) and activating protein 1 (AP-1).

In addition to cytokines, metabolites of arachidonic acid also participate in the inflammatory process. Products produced by the metabolism include both cyclooxygenase products (prostaglandins, thromboxanes) and lipooxygenase products (leukotrienes). Products such as leukotriene B4 ($LTB_4$) and prostaglandin E2 ($PGE_2$) that are representative of these two pathways can initiate PMN recruitment and changes in vascular tone and blood flow. Increased production of prostaglandins during an inflammatory response is achieved by induction of cyclooxygenase 2 (COX-2). COX-2 expression is mediated by NF-κB activation (Plummer et al., 1999, Oncogene, 18:6013–6020).

Current treatment of inflammation includes aspirin, nonsteriodal anti-inflammatories and dexamethasone. Sites of action of these compounds range from inhibition of enzymes responsible for production of arachidonic acid metabolites to inhibition of cytokine expression.

Evaluation of the active ingredients in turmeric has focused primarily on curcumin, a polyphenylic responsible for the yellow color of turmeric. In vitro studies have demonstrated that curcumin will inhibit production of inflammatory mediators, such as TNF-α and IL-1 (Chan 1995, Biochem. Pharmacol. 49:1441–1556; Chan et al., 1998, Oncogene 17:173–178; Abe et al., 1999, Pharmacol. Res. 39:41–47). In addition, curcumin has been reported to also inhibit superoxide and $PGE_2$ production and to inhibit expression of inducible nitric oxide synthase (iNOS) and COX-2 (Ruby et al., 1995, Cancer Lett. 94:79–83; Joe and Lokesh, 1997, Lipids 32:1173–1180; Chan et al., 1998; Hong et al., 2002, Ethnopharmacol. 83:153–159; and Hong et al., Planta Med. 68:545–547). For curcumin, data indicate that a major site of action is inhibition of transcription factor activation (Chan et al., 1998; Plummer et al., 1999, Oncogene 18:6013–6020: Jobin et al., 1999, J. Immunol. 163: 3473–3483; Zhang et al., 1999, Carcinogenesis 20:445–451), including NF-κB and AP-1. Additionally, Chen and Tan (1998, Oncogene 17:173–178) have also shown that curcumin can inhibit kinase activity in the c-Jun N-terminal kinase pathway. This pathway is also responsible for activation of NF-κB and AP-1 transcription factors.

While the activity and sites of action of curcumin have been studied, the potential anti-inflammatory activity of other compounds in turmeric has not been systematically examined. Other potential anti-inflammatory compounds may be present in *C. longa* extracts. For example, sesquiterpenoids from *C. xanthorrhiza* and *C. zedoaria* have been shown to inhibit COX-2 and iNOS activity at concentrations similar to those found for curcumin inhibition (Lee et al., 2002, J. Environ. Pathol. Toxicol. Oncol. 21:141–148). Because curcuminoids are only a small fraction of turmeric, it would be beneficial if other active compounds could be isolated and identifies.

SUMMARY OF THE INVENTION

It is an object of this invention to provide an anti-inflammatory preparation which does not affect COX-2 expression.

A mixture of turmeric oils includes fractions 6–10 obtained by dichloromethane-methanol (1:1 v/v) extraction followed by a gradient elution using water (A) and acetonitrile (B), the gradient comprising 0 min 40% B, 10 min 60% B, 32 min 100% B, 38 min 100% B and 40 min 40% B and chromatographically separated using a Luna C 18 (2) column with a C 18 guard column to produce fractions numbered 6–10 of FIG. 2.

A method of treating inflammation includes administering to a mammal suffering therefrom a sufficient amount of the mixture of turmeric oils to ameliorate the symptoms of arthritis. In one embodiment the inflammation is arthritis, particularly rheumatoid arthritis.

In another embodiment, there is provided a method of treating inflammation without inhibiting COX-2 expression in a mammal. The method includes administering to a mammal a sufficient amount of the mixture of turmeric oils.

In yet another embodiment, there is provided a pharmaceutical composition for treating inflammation which includes a mixture of turmeric oils and a pharmaceutically compatible excipient.

In another embodiment a nutraceutical composition for treating inflammation includes a mixture of turmeric oils.

In yet another embodiment, there is provided a mixture of turmeric oils comprising a hexane soluble fraction obtained by dissolving turmeric powder in hexane to form a hexane mixture, filtering the hexane mixture and evaporating the hexane from the turmeric oil mixture. In another embodiment, there is provided a refined turmeric oil combination that is the oil left after the turmeric oil mixture is dissolved in hexane, placed on a silica gel/hexane chromatography column, and eluted with hexane into fractions that were then evaporated, thereby leaving the refined turmeric oil combination.

In another embodiment, there is provided a method of treating inflammation in a mammal calling for providing a refined turmeric oil combination and administering the refined turmeric oil combination in sufficient quantity to treat the inflammation in the mammal. The inflammation to be treated can be arthritis. The arthritis can be rheumatoid arthritis. Alternately, the method of treating inflammation in a mammal can utilize a mixture of turmeric oils which is administered in sufficient quantity to treat the inflammation in the mammal. The inflammation to be treated can be arthritis, which can be rheumatoid arthritis.

In yet another embodiment, there is provided a pharmaceutical composition of extracted turmeric oils comprising the refined turmeric oil combination and a pharmaceutically acceptable excipient.

BRIEF DESCRIPTION OF THE DRAWINGS

FIG. 3A was obtained with the recombination of fractions 6–10 in appropriate mass ratios. FIG. 3B is a mixture isolated as a by-product of curcumin purification. The scales differ between FIGS. 3A, 3B and 2.

DETAILED DESCRIPTION OF THE PREFERRED EMBODIMENT

To test for potential anti-inflammatory activity of other turmeric components, we have prepared an organic extract. Furthermore, we have prepared and tested fractions and subfractions from this extract to test for active compounds. Anti-inflammatory activity was measured using a human promyelocytic leukemia cell line, HL-60 cells, differentiated by PMA and stimulated by LPS in vitro. Production of TNF-α and $PGE_2$ were inhibited by curcuminoids as previously reported. In addition, other fractions tested demonstrated inhibition of TNF-α and $PGE_2$ at concentrations similar to those seen for curcumin.

In order to test the anti-inflammatory activity of compounds isolated from rhizomes of *Curciuma longa* L. (Zingiberaceae), we have established an in vitro test system. HL-60 cells were differentiated and exposed to lipopolysaccharide (LPS) from *E. coli* (1 µg/ml) in the presence or absence of botanical compounds for 24 hrs. Supernatants were collected and analyzed for the production of TNF-α and $PGE_2$ by standard ELISA assays. Water-soluble extracts were not cytotoxic and did not contain biological activity. Organic extracts of turmeric were only cytotoxic at concentrations above 50 µg/ml, respectively. Crude organic extracts of turmeric were capable of inhibiting LPS induced TNF-α ($IC_{50}$=15.2 µg/ml) and $PGE_2$ ($IC_{50}$=0.92 µg/ml) production. Purified curcumin was more active than either demethoxy- or bisdemethoxycurcumin. Fractions and subfractions of turmeric extracts collected from preparative HPLC had differing biological activity, ranging from no activity to $IC_{50}$<1 µg/ml. For some fractions, subfractionation resulted in a loss of activity, indicating interaction of the compounds within the fraction to produce an anti-inflammatory effect. Combination of several of the fractions that contain the turmeric oils were more effective than the curcuminoids in inhibiting $PGE_2$. While curcumin inhibited COX-2 expression, turmeric oils had no effect on levels of COX-2 mRNA.

Definitions

Curcuminoids are compounds extracted from turmeric with ethanol. Besides curcumin, they include demethoxycurcumin and bis methoxycurcumin.

Figure 2:
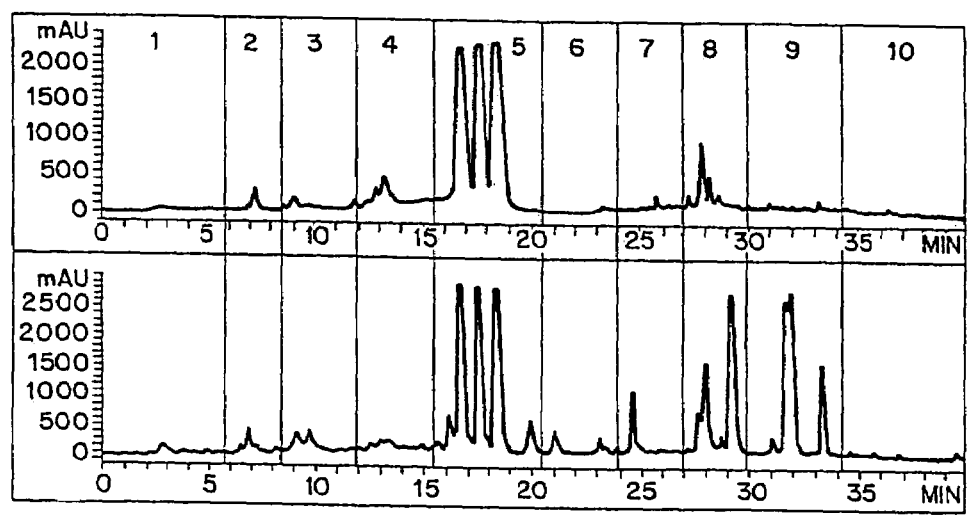
FIG. 2 is a chromatogram demonstrating the peaks present in the crude extract of turmeric. Spectra at both 425 and 250 nM are shown. As indicated on the chromatogram, the extract was subdivided into ten fractions, of which fraction 5 contains the curcuminoids.

"Turmeric oil" or "turmeric extract oil" as used herein is an extract of turmeric obtained by dichloromethane-methanol (1:1 v/v) extraction and subsequent gradient elution using water (A) and acetonitrile (B), wherein the gradient inclused 0 min 40% B, 10 min 60% B, 32 min 100% B, 38 min 100% B and 40 min 40% B and chromatographically separatedusing a Luna C 18(2) column with a C 18 guard column to produce a mixture of fractions numbered 6–10 in FIG. 2.

A "turmeric oil mixture" is prepared by dissolving turmeric powder in hexane to form a turmeric-hexane mixture, and evaporating the hexane from the turmeric oil mixture. A "refined turmeric oil combination" is prepared from the turmeric oil mixture. First, it is dissolved in hexane, then placed on a silicon gel/hexane chromatography column and elevated with hexane into fractions that were then evaporated to leave refined turmeric oil.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

The mixture turmeric oil or refined turmeric oil combination of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The products of the present invention may be formulated for administration for the treatment of a variety of conditions. In the manufacture of a pharmacuetical formulation according to the invention, the products of the present invention and the physiologically acceptable salts thereof, or the acid derivatives of either (hereinafter referred to as the "active compound") are typically admixed with, inter alia, a pharmaceutically acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active products may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal, parenteral (e.g., subcutaneous, intramuscular, intradermal, inhalational or intravenous) and transdermal administration, although the most suitable route in any given case will depend on the nature and severity of the condition being treated and on the nature of the particular active product used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, inhalational or intradermal injection. Such preparations may conveniently be prepared by admixing the compound with water or a glycine buffer and rendering the resulting solution sterile and isotonic with the blood. Alternately, the turmeric oils can be added to a parenteral lipid solution.

Formulations suitable for rectal administration are preferably presented as unit dose suppositories. These may be prepared by admixing the active compound with one or more conventional solid carriers, for example, cocoa butter, and then shaping the resulting mixture.

Formulations of the inventive mixtures are particularly suitable for topical application to the skin and preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may also be presented as medicated bandages or discrete patches adapted to remain in intimate contact with the epidermis of the recipient for a prolonged period of time. Formulations suitable for transdermal administration may also be delivered by iontophoresis (passage of a small electric current (~15 mA) to "inject" electrically charged ions into the skin) through the skin. For this, the dosage form typically takes the form of an optionally buffered aqueous solution of the active compound. Suitable formulations comprise citrate or bis/tris buffer (pH 6) or ethanol/water and contain from 0.01 to 0.2M active ingredient.

In addition to the products described herein, the present invention also provides useful therapeutic methods. For example, the present invention provides a method of reducing anti-inflammatory activity. More specifically, the present invention provides a method of treating inflammation and more particularly arthritis and specifically rheumatoid arthritis and reactive arthritis. Inflammation can aggravate lower backs, sprained joints and pulled muscles. Other conditions due to inflammation include rhinitis, Paget's disease, inflammatory bowel disease, acquired inflammatory demyelinating neuropathies and autoimmune diseases such as myasthenia gravis, thyrotoxicosis, pernicious anemia and thrombocytopenia purpura.

Subjects may be treated using the methods of the present invention and are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the mixtures of turmeric oil extracts described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.01 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active product, including the cases where a salt is employed. Typically a dosage from about 0.5 mg/kg to about 5 mg/kg will be employed for intravenous or intramuscular administration. A dosage from about 1 mg/kg to about 50 mg/kg may be employed for oral administration.

The present invention also provides medical foods comprising turmeric oil mixture or refined turmeric oil combination, at least one macronutrient selected from the group consisting of protein, carbohydrate and fat, and at least one mixture of the described turmeric extracts, the medical food being compounded for the amelioration of an inflammation-related disease. The protein source is preferably a hypoallergenic rice protein extract, suitably prepared as described in U.S. patent Ser. No. 4,876,096, incorporated herein by reference. The hypoallergenic rice protein extract is preferably fortified with at least one of the following amino acids: L-lysine, L-threonine and L-cysteine. In a presently preferred embodiment, the medical foods of the present invention are fortified with L-lysine and L-threonine in amounts of 6.3% and 0.28% of the weight of rice protein, respectively.

Both the dietary supplements and medical foods of the present invention are preferably used in powder form which can be dissolved in a liquid suitable for human consumption, such as water or a fruit juice. The dietary supplements and medical foods of the present invention can, however, be utilized in any suitable form, such as a solid bar, as a paste, gel, tablet, capsule or liquid.

Typically, the dietary supplements and medical foods of the present invention are preferably administered two times per day, preferably once in the morning and once in the afternoon. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals. A serving size for a medical food of the present invention will preferably be in the range of from about 45 grams to about 60 grams and will provide from about 180 calories to about 220 calories to the consumer. In a presently preferred treatment regimen, a person in need of treatment is provided with two servings of a medical food of the present invention per day. A presently preferred serving size is about 52 grams of powdered medical food which delivers about 200 calories to the consumer.

The MTT assay is based on the ability of a mitochondrial dehydrogenase enzyme from viable cells to cleave the tetrazolium rings of the pale yellow MTT and form a dark blue formazan crystals which is largely impermeable to cell membranes, thus resulting in its accumulation within healthy cells. Solubilization of the cells by the addition of a detergent results in the liberation of the crystals which are solubilized. The number of surviving cells is directly proportional to the level of the formazan product created.

The XTT assay is based on the ability of metabolic active cells to reduce the tetrazolium salt XTT to orange colored compounds of formazan. The dye formed is water soluble and the dye intensity can be read at a given wavelength with a spectrophotometer. The intensity of the dye is proportional to the number of metabolic active cells. The use of XTT greatly simplifies the procedure of measuring proliferation, and is, therefore, an excellent solution to the quantitating of cells and their viability without using radioactive isotopes.

The present invention is explained in greater detail in the following non-limiting examples.

EXAMPLE 1

Methods and Materials

Supplies

Turmeric (powdered rhizome of C. longa) was obtained from Botanicals International (Long Beach, Calif.). Purified curcuminoids (curcumin, demethoxycurcumin and bis-demethoxycurcumin) were kindly provided by S. D. Jolad. HL-60 cell line (ATCC, CCL-240) was purchased from ATCC (Manassas, Va.). PMA (Sigma, St. Louis, Mo., P 1585); LPS (Sigma, L2630); curcumin (Sigma, C7727); MTT {3-(4.5-dimethylthiazol-2-yl)-2,5-diphenyltetrazolium bromide} (Sigma M5655); XTT {2,3-bis (2-methoxy-4-nitro-5-sulfophenyl)-5-[(phenylamino) carbonyl]-2H-tetrazolium hydroxide} (Sigma, X4626) were all stock items. PMS (Cat No. 68600) was purchased from Fluka Biochemika (Buchs, Switzerland). IMDM medium were purchased from Gibco BRL (Division of Invitrogen, Carlsbad, Calif.). Human TNF-α and $PGE_2$ immunoassay kits were purchased from R & D systems (Minneapolis, Minn., Cat No. DTA 50 and DEO 100, respectively).

Data Collection

All data concerning plant sources, extraction procedures, chemical analysis and bioassay results were stored in a relational database (NAPIS) (White Point Systems, Friday Harbor, Wash.) for easy retrieval and searches.

HPLC Fractionation

Following dichloromethane-methanol (1:1 v/v) extraction, the components of the turmeric sample were separated by gradient method with a flow rate of 21.2 mL/min at ambient temperature. The mobile phase consisted of (A) Milli-Q reagent-grade water (Millipore, Billerica, Mass.) and (B) acetonitrile (Burdick and Jackson, Muskegon, Mich.). The following elution gradient was used: 0 min 40% B, 10 min 60% B, 32 min 100% B, 38 min 100% B; 40 min 40% B.

The 1100 series purification system consisted of two preparative HPLC pumps, a multi-wavelength detector, a solvent delivery system, and a 220 microplate sampler (Agilent Technologies, Palo Alto, Calif.). Chromatographic separation was accomplished using a Luna C 18 (2) column (5 μm, 250×21.2 mm) with a C 18 guard column (60.0 mm×21.2 mm) from Phenomenex (Torrance, Calif.). The eluent was monitored at 425 nm (signal A) and 250 nm (signal B). ChemStation for LC 3 D (Rev. A. 08.04, Agilent Technologies) with CC-Mode (Rev. A.03.02, Nederland B. V.) was used to control the separation and fractionation.

Cell Culture

HL-60 cells were cultured in Iscove's modified Dulbecco media (IMDM, with 4 mM L-glutamine, 1.5 g/l sodium bicarbonate, 20% of fetal bovine serum [FBS] at 37° C., 5% $CO_2$). Actively growing cells were distributed into 48-well plates ($1\times10^6$/mL, 0.5 mL/well) and cultured with 10 nM phorbol myristate acetate (PMA) for 24 hrs. at 37° C., 5% $CO_2$ to differentiate the cells. Cells were washed with culture media and different concentrations of extract, fractions or sub-fractions and LPS (1 µg/ml) were added. Cells were cultured for another 24 hrs. Supernatants were removed and stored at −80° C. until assayed for human TNF-α and $PGE_2$.

Immunoassay for TNF-α and PGE

Immunoassay kits were purchased from R & D Systems (Minneapolis, Minn.). Optical density (O.D.) was measured on a Spectra max plus plate reader (Molecular Devices, Sunnyvale, Calif.) at 450 nm for TNF-α and 405 nm for $PGE_2$. The reference was 570 nm. Data were analyzed using Molecular Devices plate reader software.

COX-2 Expression Assay

Levels of mRNA for COX-2 were determined using a Quantikine mRNA assay kit available from R & D Systems. Cells were stimulated with LPS in the absence or presence of the botanical extracts. At 24 hrs., cells were lysed and total RNA was isolated using Qiagen kits (Valencia, Calif.). RNA samples were processed and added to the reagents as described in the manufacturer's instruction. Values were compared against a standard curve. Data were recorded as percent of LPS alone (LPS alone=100%). Preliminary tests showed that COX-2 expression reached a plateau at 4 hrs after LPS stimulation. However, since these same levels of expression were maintained for 24 hrs, data were collected at 24 hrs for correlation with $PGE_2$ production measurements.

Cytotoxicity Assay

HL-60 cells were cultured as described above. Cells ($1\times10^5$ cells/mL) were distributed to 96-well plates, 0.1 mL/well and cultured with PMA (10 nM) for 24 hrs. Cells were washed with culture medium and different concentrations of extract, fractions or sub-fractions, and LPS (1 µg/mL) were added. Cells were cultured for another 24 hrs. After that, for MTT assay, 20 µL of MTT (5 mg/mL) were added to each well and plates were cultured for another 4 hrs. Supernatants were aspirated and 100 µL of isopropanol-HCl (0.04% HCl) were added to each well. The plates were protected from the light at room temperature overnight. The O.D. was measured at 570 nm (with 660 nm as the reference wavelength). For XTT assay, 25 µL of XTT (1 mg/mL with PMS) were added to each well and the plates were cultured for another 4 hrs. in the dark. O.D. was measured at 450 nm (with 650 nm as the reference wavelength).

Results

Figure 1:
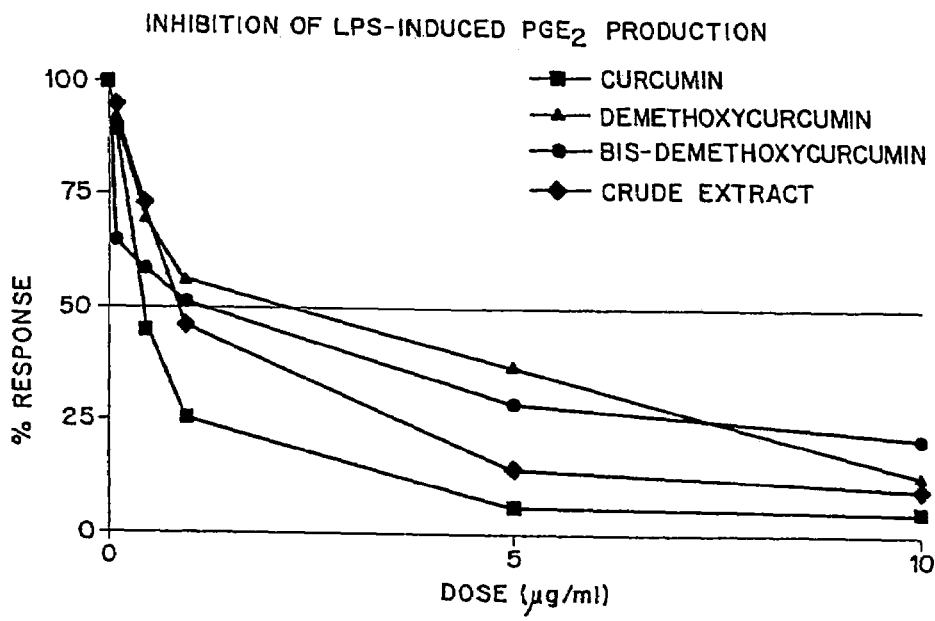
FIG. 1 is a dose-response curve for inhibition of LPS-induced $PGE_2$ production. HL-60 cells were cultured for 24 hrs. in the presence of 1 µg/ml of LPS and various concentrations of turmeric compounds. Supernatants were analyzed for production of $PGE_2$ by standard ELISA. All values were normalized to LPS alone values=100%. $IC_{50}$ concentrations are where the curves cross the 50% lines.

Turmeric sample (C. longa) extracted with dichloromethane-methanol (1:1 v/v) inhibited LPS-induced production of TNF-α and $PGE_2$ (FIG. 1). The concentration at which there was a 50% inhibition of protein production ($IC_{50}$) was 15.2 fg/mL for TNF-α and 0.92 µg/mL for $PGE_2$. Water soluble extracts had no biological activity. Cytotoxicity was only seen at levels above 50 µg/mL.

Preparative HPLC separation of the above crude extract was performed and provided ten fractions. The 425/250 nm chromatograms are shown in FIG. 2, with the ten separate fractions indicated. The three major peaks in fraction 5 are the three curcuminoid compounds: curcumin (RT: 18.4 min), demethoxycurcumin (RT: 17.5 min) and bis-demethoxycurcumin (RT: 16.7 min). This fraction accounted for 32.2% of the mass of the ten fractions. Each of these three compounds was separated, purified and tested separately for its ability to inhibit LPS-induced inflammatory mediator production. FIG. 1 shows that all three compounds were effective in inhibiting LPS-induced $PGE_2$ production. Of the three, the most active was curcumin, followed by bisdemethoxy- and demethoxycurcumin. These compounds were also effective at inhibiting TNF-α production, but at significantly higher concentrations (Table 1).

TABLE 1

$IC_{50}$ of Curcuminoids from Fraction 5 of Turmeric Extract

|  | Curcumin | Demethoxy-curcumin | Bisdemethoxy-curcumin |
|---|---|---|---|
| TNF-α | 28.8 | 24.7 | 24.6 |
| $PGE_2$ | 0.45 | 2.6 | 1.2 |

Values are concentrations of each chemical required to lead to 50% inhibition of LPS-induced mediator production. Values are in µg/mL.

We investigated whether differences in TNF-α and $PGE_2$ $IC_{50}$ values in our experiments were due to loss of curcumin from the medium as has been reported (Wang et al., 1997, J. Pharmaceut. Biomed. Anal. 15:1867–76). The curcumin standard was placed in IMDM media and incubated for 24 hrs. under our culture conditions. Aliquots were collected and sampled for curcumin. Concentrations recovered after 24 hrs. were 90–95% of the original concentration. Therefore, curcumin was not lost during incubation.

Besides the curcuminoids, other fractions isolated from the original extract also had significant activity. $IC_{50}$ data for each of the ten fractions is shown in Table 2. Several fractions (2–4) showed lower $IC_{50}$ values for inhibition of TNF-α production than did the curcuminoids (fraction 5). In addition, the $IC_{50}$ values for inhibition of $PGE_2$ were within the same order of magnitude, regardless of the fraction tested. The percentage of the total mass in each fraction is shown in Table 3. Fractions 6–10 accounted for 38.8% of the total weight of all extract fractions.

TABLE 2

$IC_{50}$ of 10 Primary Fractions from Turmeric Extract Oil

|  | 1 | 2 | 3 | 4 | 5 | 6 | 7 | 8 | 9 | 10 |
|---|---|---|---|---|---|---|---|---|---|---|
| TNF-α | 29.2 | 6.5 | 5.8 | 11.7 | 18.9 | 39.4 | — | 26.7 | 25.6 | — |
| $PGE_2$ | 2.2 | 4.7 | 3.5 | 1.0 | 0.9 | 3.7 | 7.5 | 1.7 | 6.3 | 6.3 |

Values are concentrations of each fraction required to provide 50% inhibition of LPS-induced mediator production. Dashes indicate no inhibitory activity for that fraction. Values are in µg/mL.

TABLE 3

Mass of Fractions Isolated from Crude Turmeric Extract Oil (T 1-1-F0)

| T 1-1-F 0 2.0611 g/20 mL (5 mL loop, 17 injections) (mg) | Total amount (mg) | % |
|---|---|---|
| TP1/08_1 | 148.5 | 10.2 |
| TP1/08_2 | 60.6 | 4.2 |

TABLE 3-continued

Mass of Fractions Isolated from Crude Turmeric Extract Oil (T 1-1-F0)

T 1-1-F 0
2.0611 g/20 mL
(5 mL loop, 17 injections) (mg)

| | Total amount (mg) | % |
|---|---|---|
| TP1/08_3 | 69.4 | 4.8 |
| TP1/08_4 | 141.8 | 9.8 |
| TP1/08_5 | 467.3 | 32.2 |
| TP1/08_6 | 48.2 | 3.3 |
| TP1/08_7 | 57.2 | 3.9 |
| TP1/08_8 | 171.0 | 11.8 |
| TP1/08_9 | 202.6 | 14.0 |
| TP1/08_10 | 83.6 | 5.8 |
| Total | 1,450.2 | |
| Recovery % | | 70.4 |

In order to further isolate the active compounds, fractions 1, 2 and 8 were subfractionated. While no large apparent peak was seen at 425/250 nm in fraction 1, this fraction nevertheless made up over 10% of the mass. Eight subfractions (A–H) from fraction 1 were isolated and tested for activity (Table 4). The majority of the activity resided in subfraction F, with an $IC_{50}$ for TNF-α of 9.9 µg/mL and for $PGE_2$ of 2.8 µg/mL. All the other subfractions had little or no inhibitory activity.

TABLE 4

$IC_{50}$ of 8 Subfractions from Fraction 1 of Turmeric Extract Oil

| | A | B | C | D | E | F | G | H |
|---|---|---|---|---|---|---|---|---|
| TNF-α | — | — | — | — | — | 9.9 | — | — |
| $PGE_2$ | — | — | 40.3 | — | 31.4 | 2.8 | 47.8 | — |

Values are concentrations of each fraction required to give 50% inhibition of LPS-induced mediator production. Dashes indicate no inhibitory activity for that fraction. Values are in µg/mL.

Fractions 2 and 8 were each subfractionated into five (A–E) and eight (A–H) subfractions, respectively (Tables 5 and 6). In both cases, none of the subfractions showed greater activity than the parent fraction, indicating that compounds in this fraction may interact to inhibit mediator production.

TABLE 5

$IC_{50}$ of 5 Subfractions from Fraction 2 of Turmeric Extract

| | A | B | C | D | E |
|---|---|---|---|---|---|
| TNF-α | — | — | 30.1 | — | — |
| $PGE_2$ | 44.0 | 9.3 | 14.0 | 25.5 | 21.7 |

Values are concentrations of each fraction required to provide 50% inhibition of LPS-induced mediator production. Dashes indicate no inhibitory activity for that fraction. Values are in µg/mL.

TABLE 6

$IC_{50}$ of 8 Subfractions from Fraction 8 of Turmeric Extract Oils

| | A | B | C | D | E | F | G | H |
|---|---|---|---|---|---|---|---|---|
| TNF-α | — | — | 35.1 | — | — | — | — | — |
| $PGE_2$ | — | 36.5 | 9.9 | — | 8.7 | 16.4 | 7.4 | — |

Values are concentrations of each fraction required to provide 50% inhibition of LPS-induced mediator production. Dashes indicate no inhibitory activity for that fraction. Values are in µg/mL.

Figure 3A:
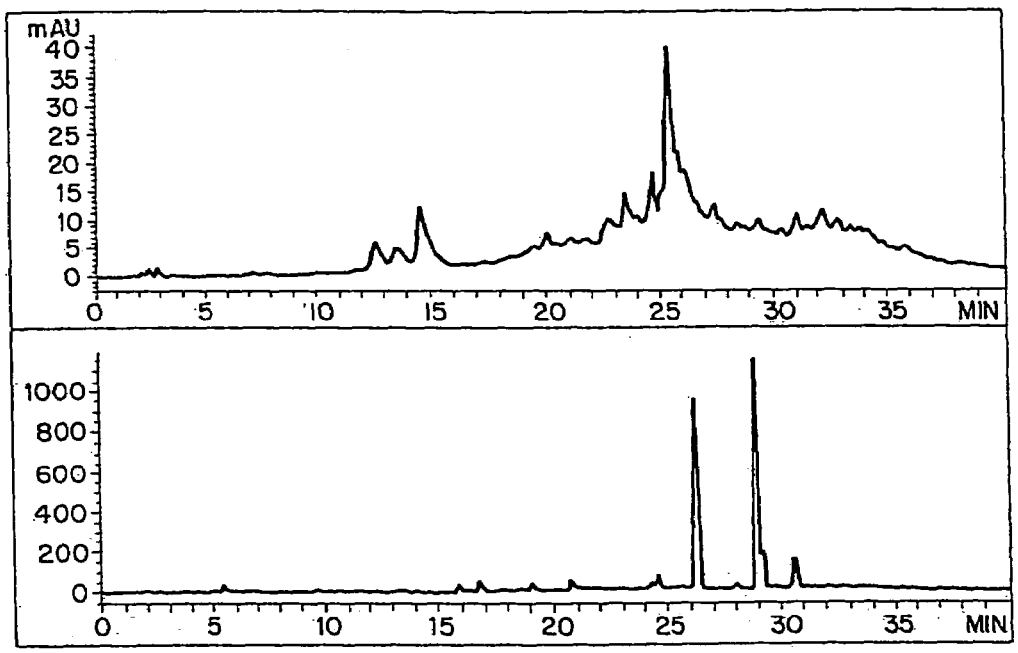
FIGS. 3A and 3B are chromatograms.

In order to further characterize the effect of interaction of compounds, we analyzed the compounds in Fractions 6–10 that were combined in the mass ratios found in the crude extracts. These fractions contain the turmeric oils. The chromatogram for these combined fractions is shown in FIG. 3A. The fraction consists primarily of two major peaks seen in the UV range, but other minor peaks are also evident. Note the change in scale of the visible chromatogram compared to FIG. 2. Combination of fractions 6–10 resulted in $IC_{50}$ values that were lower than or equivalent to those of the curcuminoids. The $IC_{50}$ for TNF-α was 7.23 µg/mL and the $IC_{50}$ for $PGE_2$ was 0.47 µg/mL.

Figure 3B:
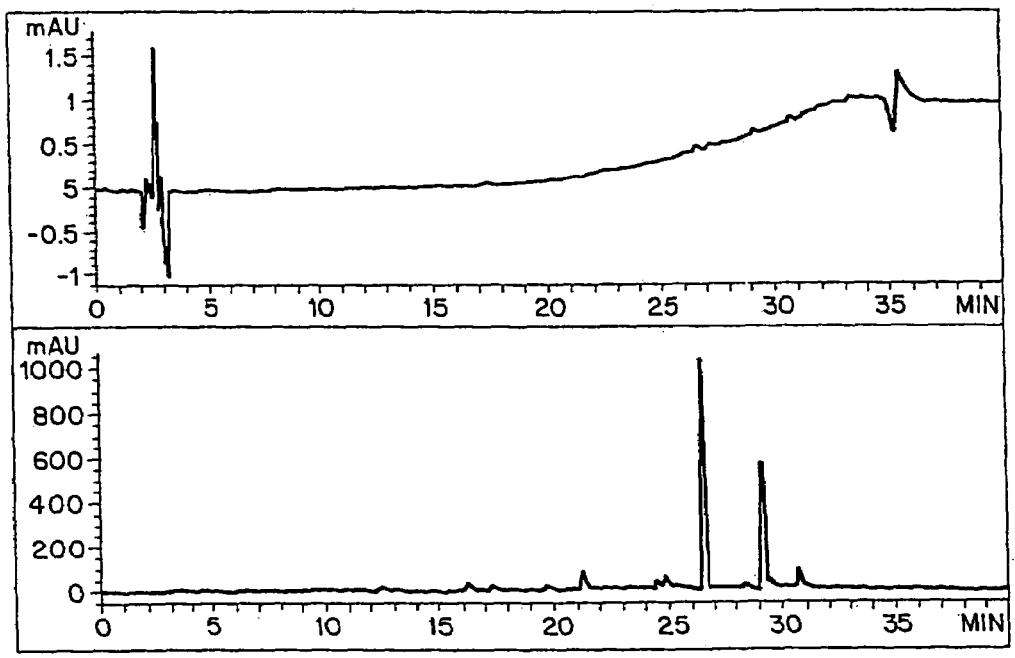

A similar mixture of compounds was also isolated as a byproduct of the isolation of the curcuminoids, as shown in FIG. 3B. The $IC_{50}$ values for LPS-induced TNF-α production for this mixture was 17.32 µg/mL. This mixture was extremely effective at inhibiting LPS-induced $PGE_2$ production, with an $IC_{50}$ for $PGE_2$ of 0.084 µg/mL. In comparison, indomethacin had an $IC_{50}$ of 0.052 µg/mL in our assay system, indicating that the effectiveness of fractions 6–10 at inhibiting LPS-induced $PGE_2$ production approached the effectiveness of a commercially available nonsteriodal anti-inflammatory compound.

It is possible that a portion of the inhibition caused by fractions 6–10 was due to binding or sequestering of LPS. Such binding would decrease the concentration and effect of LPS stimulation concentration and could be confused with an inhibited production of $PGE_2$ or TNF-α. This possibility was tested by using zymosan stimulation in place of LPS. Inhibition of opsonized zymosan-induced $PGE_2$ production occurred at concentrations equivalent to those seen with LPS stimulation. Therefore, LPS was not bound by compounds in fractions 6–10.

Figure 4:
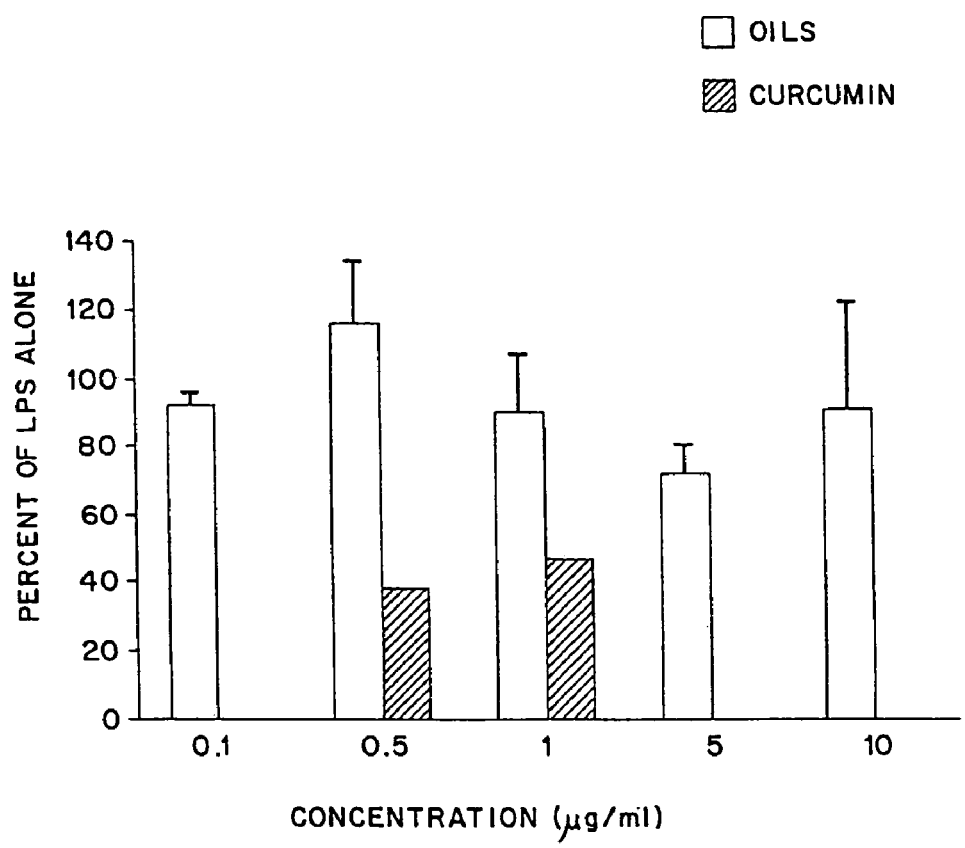
FIG. 4 is a bar graph showing the degree of inhibition of COX-2 expression by curcumin and turmeric oils. HL-60 cells were stimulated with LPS in the presence of curcumin or turmeric oils (fractions 6–10). Curcumin at 0.5 and 1.0 µg/ml resulted in greater than 50% inhibition of COX-2 expression. However, turmeric oils did not show any significant inhibition of COX-2 expression. Values are expressed as a percentage of COX-2 expression following LPS stimulation alone.

Previous reports have shown that curcumin inhibits expression of inflammatory mediators by inhibiting activation of transcription factors responsible for inflammatory gene expression. Inhibition of $PGE_2$ by curcumin is therefore believed to be due to inhibition of COX-2 expression. However, only limited data exist on the site(s) of inhibition of $PGE_2$ production by turmeric oils. HL-60 cells were exposed to LPS in the presence of curcumin or turmeric oils (fractions 6–10). Cells were lysed and mRNA was collected and analyzed for COX-2 messages. Values were expressed as a percentage of LPS alone (100%). Data are shown in FIG. 4. As expected curcumin at concentrations as low as 0.5 µg/mL resulted in a greater than 50% decrease in COX-2 expression. However, even at concentrations up to 10 µg/mL, turmeric oils did not cause a significant decrease in COX-2 expression.

Discussion

The powdered rhizome of the herb *Curcuma longa* L. (Zingiberaceae) has been used extensively in the Ayurvedic medicine to treat inflammation, skin wounds and tumors (Ammon and Wahl, 1991, Planta Med., 57:1–7). The best known turmeric compound is curcumin, which has been shown to alter the production of numerous cytokines and inflammatory mediators. The wide range of actions of curcumin is most likely due to its interaction and inhibition of transcription factor activation, specifically in the NFκB and AP-1 pathways.

Curcumin is known to produce 50% decreases in production of TNF-α at concentrations ranging from 2–10 μg/mL (Chan et al., 1995, Biochem. Pharmacol. 49:1551–1556; Abe et al., 1999, Pharmacol. Res. 39:41–47). $IC_{50}$ values for inhibition of $PGE_2$ and/or COX-2 expression are in the same range (Zhang et al., 1999, Carcinogenesis 20:445–451; Goel et al., 2001, Cancer Lett. 172:111–118). Data disclosed herein for inhibition of $PGE_2$ are similar to the reported values. However, inhibition of TNF-α only occurred at concentrations that were an order of magnitude higher than those inhibiting $PGE_2$. Production of both TNF-α and $PGE_2$ depend on induction of their gene expression by activation of transcription factors (Jobin et al., 1999, J. Immunol. 163:3474–3483). Previous research has demonstrated that curcumin inhibited these pathways at steps upstream of the activation of the transcription factors. This should result in similar $IC_{50}$ values for mediators that are induced through similar pathways.

It is possible that the timing of application of the curcumin may differentially affect the expression of the two mediators. Curcumin is most effective at inhibiting NF-κB activation if it is added an hour prior to inflammatory stimulation (Singh and Aggarwal, 1995, J. Biol. Chem. 270:24995–25000). If activation of TNF-α gene expression occurs more rapidly than up-regulation of COX-2, different levels of inhibition could occur following simultaneous addition of stimulus and inhibitor, as was done herein. Direct COX-2 inhibition by anti-inflammatory compounds may also contribute to the lower $IC_{50}$ for $PGE_2$ herein (Zhang et al., 1999, Carcinogenesis 20:445–451).

The curcuminoids are three primary compounds seen in the crude extract from the rhizome (FIG. 2). We isolated each compound (curcumin, demethoxycurcumin and bisdemethoxycurcumin) and analyzed each separately to evaluate anti-inflammatory potential. All three compounds inhibited $PGE_2$ production in the range of 0.5 to 2.5 μg/mL $IC_{50}$, with curcumin being the most effective. Both Ramsewak et al. (2000, Phytomedicine 7:303–308) and Kim et al. (2001, Neurosci. Lett. 303:57–61) have compared the activity of all three curcuminoids. In assays to test the direct inhibition of COX-2 enzyme activity, Ramsewak et al. (2000, Phytomedicine 7:303–308) found that bisdemethoxycurcumin was the most effective and that curcumin only resulted in a slight inhibition of the enzyme activity. Ramsewak analyzed inhibition of COX-2 at concentrations of 125 mg/mL, values that are significantly higher than the $IC_{50}$ values shown herein for $PGE_2$ production and COX-2 mRNA expression. Therefore, it is unlikely that the curcuminoids exert their major action through direct inhibition of the COX-2 enzyme, but rather through inhibition of its expression. $IC_{50}$ values for antioxidant activity for the curcuminoids were similar but an order of magnitude higher than those reported here (Kim et al, 2001, Neurosci. Lett. 303:57–61).

In addition to the curcuminoids, other fractions isolated from the crude rhizome extract showed significant inhibition of LPS-induced $PGE_2$ production. Specifically the combination of fractions 6–10, which contains the turmeric oils, had an $IC_{50}$ of 84 ng/mL, a value approaching that for indomethacin. Hong et al (2002, Planta Med. 68:545–547) and Lee et al (2002, J. Environ. Pathol. Toxicol. Oncol. 21:141–148) have reported that sesquiterpenoids (β-tumerone, ar-tumerone and xanthorrhizol) isolated from *Curcuma zedoaria* and *Curcuma xanthorrhiza* can inhibit $PGE_2$ production with $IC_{50}$ values in the range of 2 to 5 μg/mL. These $IC_{50}$ values are similar to those we have seen for individual fractions 6–10 (Table 2). Lee et al (2002, ibid.) showed inhibition of COX-2 expression by xanthorrhizol at concentrations above 5–10 μg/mL. However, the $IC_{50}$ values were not reported. This inhibition contrasts with findings herein. Exposure to the 6–10 fractions produced no significant reduction in COX-2 mRNA levels up to 10 μg/mL, even though $PGE_2$ $IC_{50}$ values of the curcuminoid purification by-product were 84 ng/mL. These data suggest that fractions 6–10 (turmeric oils) and similar curcuminoid purification by-product inhibited $PGE_2$ production by either direct inhibition of the COX-2 enzyme or by some other mechanism downstream from induction of COX-2 expression. Fractions 6–10, in isolation, demonstrated $PGE_2$ $IC_{50}$ values in the 2–6 μg/mL range.

However, together these fractions exerted more potent inhibition of $PGE_2$ production. This implies a synergy between two or more of the chemicals in these fractions. Synergy could be produced in several different ways, including, but not limited to the following: For example, combination of the fractions could result in better bioavailability of the active compound(s) inside the cell. In addition, several of the compounds could act at different sites in the transduction involved in LPS-induced expression of COX-2. Or finally, some of the compounds could inhibit COX-2 expression, while others directly inhibit the enzyme activity. These are only a few of the potential mechanisms that could lead to the synergy, and this patent should not be limited by the particular mechanism.

In conclusion, compounds isolated from *Curcuma longa* rhizomes inhibited inflammatory mediator production in vitro. These compounds included the curcuminoids and the turmeric oils. The most effective compounds were mixtures of several of the turmeric oil fractions and the curcuminoid purification by-product. Different mechanisms of action appear to apply with curcumin inhibiting COX-2 expression and the turmeric oils apparently act at some point downstream of COX-2 expression.

EXAMPLE 2

In another method for isolating crude essential oil of turmeric, commercially processed dry turmeric powder (1 kg) was placed in a 5 L stainless steel container equipped with a lid and mechanical stirrer. Then n-hexane (3.5 L, or 3.5 mL/g of turmeric powder) was poured into the container containing turmeric, and the mixture was gently stirred at room temperature for 24 hours. The mixture was then filtered through a fritted funnel (coarse porosity, 4 L size) under vacuum. After completion of filtration, the marc was washed with fresh n-hexane (about 1 L). Lastly, solvent from the combined filtrate and washing was stripped off under vacuum using a rotary evaporator, and the resulting crude essential oil was left under vacuum for a minimum period of 24 hrs. for a yield of 27.3 g, or 2.7% of the total weight of the turmeric powder.

EXAMPLE 3

A column chromatography procedure was devised for obtaining a refined turmeric oil combination. The following equipment and materials were used. A glass column (burette) had 3.5" (w)×15" (h) dimensions and was fitted with frit support (porosity C) and a Teflon stopcock. The silica gel was obtained from Scientific Adsorbents Inc. (SAI) (Cat. # 02826–25; Lot # B05R3-17, with a particle size of 32–63 µm and a pore size of 60 The solvents were n-hexane (AR grade) and ethyl acetate (AR grade).

The silica gel was packed by the slurry pack method. A pourable slurry of silica gel (140 g, 5 g/g oil) was prepared in a 1 L wide-mouthed bottle by soaking in sufficient amount of n-hexane for 2 hrs. at room temperature (RT). The slurry was then poured rapidly into the column and clamped vertically. The slurry was allowed to gel and settle down firmly under gravity. The stopcock was opened to remove excess solvent and then closed when the solvent reached the surface of the silica gel. The sample was applied by the wet load method. Crude essential oil from the preceding description was dissolved in 50 Ml n-hexane and carefully placed on top of the packed silica gel column and allowed to adsorb. The adsorbed material was covered with a small layer of silica gel (approximately 1 cm).

Elution was by the gravity method. The column was eluted with n-hexane (100%). Fractions (25–30 Ml each) were collected until the color of the elute changed from colorless to yellow to colorless again. The column was then eluted with a mixture of n-hexane-ethyl acetate (17:1 v/v) for a total of 15 L. The column was finally leached with 100% ethyl acetate (1 L) and elution was discontinued. The solvent from the 15 L fraction collected in the yellow fraction was stripped off under vacuum using a rotary evaporator, and the resulting refined essential oil was then left under vacuum for a minimum of 24 hrs. The yield was 20 g, or 73.8%.

EXAMPLE 4

In Vivo Testing

For in vivo testing, the Streptococcal cell wall (SCW) model of arthritis is the model of choice for delineating the role of specific hormones and cytokines in joint inflammation. SCW-induced arthritis in Lewis rats is used as a surrogate for arthritis in humans. Lewis rats are particularly susceptible to arthritis and show well characterized pathologic manifestations of SCW-induced arthritis. Lewis rats are widely used as an animal model for rheumatoid arthritis.

More recently, because bone resorption in the SCW model had previously been described, but had not been well characterized in this model, we have also used a small-animal bone densitometer to verify the usefulness of this model for studying inflammation-associated bone resorption and destruction. Consistent with other animal models of arthritis, and with rheumatoid arthritis in humans, the chronic phase of joint swelling in SCW arthritis was accompanied by a 24% decrease in femoral bone mineral density (BMD) (Funk et al., 2003, Arthr. Rheum. 48:1721–31).

A single intraperitoneal injection of an aqueous suspension of cell wall isolated from group A streptococcal bacteria (SCW) is given to Lewis rats. The arthritis occurs in two phases: an acute phase, full blown at day 3 and mainly due to joint swelling and inflammation, and a chronic phase starting at about 14 days and analyzed at 30 days with actual joint destruction. Additionally, granulomas form in the spleen and liver in response to local SCW deposition. Rats are treated daily with botanicals by oral gavage (po), intraperitoneal (ip) injection, or subcutaneous (sc) administration beginning 4 days prior to treatment with SCW (SCW+ turmeric oil, n=12/group). An arthritis control group is treated with drug vehicle alone in a similar fashion (SCW+ vehicle, n=12). To determine the effects of turmeric oil on primary outcomes (i.e., BMD) independent of the involvement of arthritis, two additional groups of animals do not receive SCW, but are treated with turmeric oil (botanical, n=5) or vehicle alone (vehicle, n=5/group). Animals are then observed daily for 30 days for the development of arthritis and scored numerically for the degree of joint swelling and erythema. Additionally, bone mineral density (BMD) is measured non-invasively at 5 specific time points throughout the 30-day course of the experiment by use of a single body scan of anesthetized animals using a Piximus densitometer (Wipro/GE Medical Systems, Waukesha, Wis.). After 30 days, animals are sacrificed. Hind and forepaws are harvested for histologic evaluation and, in some cases, measurement of bone mineral density in excised femurs; liver and spleen are harvested for histologic assessment of granuloma formation; and blood is drawn for assessment of serum markers of inflammation, serum markers of bone and cartilage destruction, renal and liver function, and white blood cell counts. In addition, some animals are sacrificed at earlier time points so that joints can also be assessed during the acute phase of the arthritic process (day 3) and just prior to onset of the chronic phase (day 14) by histopathological evaluation; organs can be assessed at the start of granuloma formation (days 3 and 14 for spleen and liver, respectively); and blood levels of inflammatory markers, joint destruction and immune cells can be correlated with disease activity. In all cases, the effect of turmeric oils on the above indices of disease activity is to be determined and compared with those obtained in animals receiving vehicle alone. Animals receive multiple ip or sc injections or botanicals by gavage (po), develop arthritis and granulomas, have BMD measurements, and have tissue harvested at the time of sacrifice.

For statistical analysis, 12 animals are required per arthritis group/5 animals per non-arthritis group, with 4 experimental groups per product to be tested [vehicle, n=5; botanical, n=5; SCW, n=12; SCW+botanical, n=12]. Two products are tested per experiment to minimize duplication of vehicle alone and SCW groups (vehicle, n=5; product 1, n=5; product 2, n=5; SCW, n=12; SCW+product 1; n=12; SCW+ product 2, n=12). Ten different botanical fractions (e.g. 3 different curcuminoids, turmeric oils, separate fractions of gingerols, unfractionated whole extracts, etc., as indicated by in vitro experiments) are tested. Effects of oral administration are compared with ip or sc dosing (2 routes of administration per product). Drugs to be administered include SCW (non-infectious) ip; turmeric oils, curcuminoids, essential oils, gingerols, ginger extract, vehicle alone (DMSO ip or sc or sesame oil po) The amount and route of administration (aside from SCW 25 µg/g) for each botanical dose is to be determined based on in vitro studies and previously published in vivo studies—e.g., curcuminoids, 200 mg/kg/day). In addition, animals receive an acetaminophen dose of 100–305 mg/kg po in drinking water for 4–6 hrs. on an ad lib basis.

At the end of the study, the animals are given an overdose of barbiturate or other euthanasia solution, such as pentobarbital 30–40 mg/kg or Telazol (a combination of tiletamine and zolazepam) 60–80 mg/kg ip.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A turmeric oil extract for treating inflammation comprising fractions 6–10 obtained by dichloromethane-methanol (1:1 v/v) extraction followed by a gradient elution using water (A) and acetonitrile (B), the gradient comprising 0 min 40% B, 10 min 60% B, 32 min 100% B, 38 min 100% B and 40 min 40% B and chromatographically separated using a Luna C 18 (2) column with a C 18 guard column to produce Fractions numbered 6–10, wherein Fractions 6–10 do not contain curcuminoids and comprise about 38.8% of the total mass of all extract fractions that elute off of the column.

2. A method of treating inflammation, the method comprising administering to a mammal suffering therefrom a sufficient amount of a turmeric oil extract to ameliorate the symptoms of inflammation, wherein the extract comprises Fractions 6–10 obtained by dichloromethane-methanol (1:1 v/v) extraction followed by a gradient elution using water (A) and acetonitrile (B), the gradient comprising 0 min 40% B, 10 mm 60% B, 32 min 100% B, 38 min 100% B and 40 mm 40% B and chromatographically separated using a Luna C 18 (2) column with a C 18 guard column to produce Fractions numbered 6–10, and wherein the extract does not contain curcuminoids and comprises about 38.8% of the total mass of all extract fractions that elute off of the column.

3. The method of claim 2 wherein the inflammation is arthritis.

4. The method of claim 3 wherein the arthritis is rheumatoid arthritis.

5. A method of treating inflammation without inhibiting COX-2 expression in a mammal, the method comprising administering to a mammal a sufficient amount of a turmeric oil extract to ameliorate the symptoms of inflammation, wherein the extract comprises Fractions 6–10 obtained by dichloromethane-methanol (1:1 v/v) extraction followed by a gradient elution using water (A) and acetonitrile (B), the gradient comprising 0 min 40% B, 10 min 60% B, 32 min 100% B, 38 min 100% B and 40 min 40% B and chromatographically separated using a Luna C 18 (2) column with a C 18 guard column to produce Fractions numbered 6–10, and wherein the extract does not contain curcuminoids and comprises about 38.8% of the total mass of all extract fractions that elute off of the column.

6. A pharmaceutical composition for treating inflammation comprising a turmeric oil extract and a pharmaceutically compatible excipient, wherein the extract comprises Fractions 6–10 obtained by dichloromethane-methanol (1:1 v/v) extraction followed by a gradient elution using water (A) and acetonitrile (B), the gradient comprising 0 min 40% B, 10 min 60% B, 32 min 100% B, 38 min 100% B and 40 min 40% B and chromatographically separated using a Luna C 18 (2) column with a C 18 guard column to produce Fractions numbered 6–10, and wherein the extract does not contain curcuminoids and comprises about 38.8% of the total mass of all extract fractions that elute off of the column.

7. A nutraceutical composition for treating inflammation comprising a turmeric oil extract, wherein the extract comprises Fractions 6–10 obtained by dichloromethane-methanol (1:1 v/v) extraction followed by a gradient elution using water (A) and acetonitrile (B), the gradient comprising 0 min 40% B, 10 min 60% B, 32 min 100% B, 38 min 100% B and 40 min 40% B and chromatographically separated using a Luna C 18 (2) column with a C 18 guard column to produce Fractions numbered 6–10, and wherein the extract does not contain curcuminoids and comprises about 38.8% of the total mass of all extract fractions that elute off of the column.

* * * * *